United States Patent
Ingram et al.

(10) Patent No.: US 10,806,917 B2
(45) Date of Patent: Oct. 20, 2020

(54) VENTED CONNECTOR FOR MEDICAL FLUID VESSELS

(71) Applicant: NEOMED, INC., Woodstock, GA (US)

(72) Inventors: Aaron N. Ingram, Canton, GA (US); Benjamin Martin Davis, Woodstock, GA (US); Mark M. Costello, County Mayo (IE); Tony Doherty, County Mayo (IE); John Burke, County Roscommon (IE)

(73) Assignee: NeoMed, Inc., Woodstock, GA (US)

( * ) Notice: Subject to any disclaimer, the term of this patent is extended or adjusted under 35 U.S.C. 154(b) by 0 days.

(21) Appl. No.: 16/393,144

(22) Filed: Apr. 24, 2019

(65) Prior Publication Data

US 2019/0255311 A1    Aug. 22, 2019

Related U.S. Application Data

(63) Continuation of application No. 14/844,956, filed on Sep. 3, 2015, now Pat. No. 10,668,263.

(60) Provisional application No. 62/192,614, filed on Jul. 15, 2015, provisional application No. 62/047,389, filed on Sep. 8, 2014.

(51) Int. Cl.
    *A61M 39/10* (2006.01)
    *A61J 1/14* (2006.01)
    *A61M 39/20* (2006.01)

(52) U.S. Cl.
    CPC ............ *A61M 39/10* (2013.01); *A61J 1/1412* (2013.01); *A61M 39/20* (2013.01); *A61M 2039/205* (2013.01)

(58) Field of Classification Search
    CPC .. A61M 39/10; A61M 39/1011; A61M 39/20; A61M 2039/205; A61M 2039/1083; A61M 2039/1088; A61M 2039/0036; A61M 2039/266; A61M 25/04; A61M 2039/10; A61M 2039/1033; A61M 2039/1038; A61M 2039/1027; A61M 2039/1066; A61J 1/1412
    See application file for complete search history.

(56) References Cited

U.S. PATENT DOCUMENTS

2003/0032940 A1*  2/2003  Doyle ................. A61M 39/045
                                                         604/533
2006/0161115 A1*  7/2006  Fangrow ............... A61M 39/22
                                                         604/249

* cited by examiner

Primary Examiner — Kevin C Sirmons
Assistant Examiner — Tezita Z Watts
(74) Attorney, Agent, or Firm — Dority & Manning, P.A.

(57) ABSTRACT

A connector for medical fluid vessels includes a fluid-seal fitting such as a male plug defining a lumen and mating with a cooperating connector, a mechanical fastener such as a screw thread for mating with the cooperating connector, and an outer housing positioned around the plug to form an annular space. Optionally, a cap can be provided with a fluid-seal fitting such as a male plug for mating with the lumen of the connector. The connector includes one or more vent openings for drainage and air-drying of any residual fluid in the annular space when capped, as well as for breaking a vacuum to prevent fluid backflow and thus ensure more accurate dosing. In some embodiments, the vent openings are provided in the outer housing. And in some embodiments, the vent openings are provided in the cap.

15 Claims, 6 Drawing Sheets

VENTED CONNECTOR FOR MEDICAL FLUID VESSELS

CROSS-REFERENCE TO RELATED APPLICATIONS

This application claims the priority benefit of U.S. Provisional Patent Application Ser. No. 62/047,389 filed Sep. 8, 2014, and U.S. Provisional Patent Application Ser. No. 62/192,614 filed Jul. 15, 2015, the entireties of which are hereby incorporated herein by reference for all purposes.

TECHNICAL FIELD

The present invention relates generally to medical devices, and more particularly to connectors for vessels for fluids in the medical field.

BACKGROUND

Healthcare patients are commonly given fluids such as medication and nutrients by being connected to fluid-delivery systems via fluid vessels. Common fluid vessels for delivering such fluids include small-bore tubes and catheters. A problem arises when these fluid tubes are misconnected. That is, when a tube from one fluid delivery system is connected to a tube intended for connection to another fluid delivery system that serves a completely different function, for example, when a feeding administration set is inadvertently connected to a tracheostomy tube. Such tubing misconnections are also referred to as LUER misconnections, small-bore misconnections, and/or wrong-route errors. Tubing misconnections have resulted in patient injuries and/or deaths, and are widely recognized as underreported.

An underlying cause of these misconnections has been attributed to the universal design of LUER connectors, which are one of the most commonly used types of small-bore connectors in healthcare. These connectors are used to couple the tubing of one medical device to another. However, the simple design and ease of use of LUER connectors allows the tube of the device of one delivery system to be connected to a tube of an unrelated system that has a different intended use (e.g., vascular, enteral, respiratory, epidural, or intrathecal), resulting in healthcare providers inadvertently connecting wrong systems together and thereby causing liquids (e.g., medications or enteral feedings) or gases (e.g., oxygen) to be delivered through the wrong route.

Efforts are underway to develop standards, such as the ISO 80369 standards, for tubing connections. These standards hold the promise of significantly addressing the tubing-misconnection problem. For example, these standards provide for a new connector for enteral feeding tubes that prevents misconnection to non-enteral connectors. This new enteral-only tube connector is also referred to as the ENFIT connector.

Yet there remain other opportunities for improving these and other connectors. For example, the new ENFIT connector for enteral feeding tubes includes an outer housing that could retain feeding liquids and thereby allow for bacteria colonization. This can result in unsanitary conditions that can inadvertently contaminate feeding fluids later delivered to the patient through the degraded ENFIT connector.

Accordingly, it can be seen that needs exist for improved connectors for fluid tubes to reduce the risk of bacteria colonization. It is to the provision of solutions to this and other needs that the present invention is primarily directed.

SUMMARY

In example embodiments, the present invention relates to individual connectors as well as connector-sets (of individual connectors) for coupling together two medical-fluid vessels. The connectors and connector-sets advantageously provide for drainage and air-drying of any residual fluid that might otherwise be retained and result in bacteria colonization, as well as for breaking a vacuum to prevent fluid backflow and thus ensure more accurate dosing.

In one aspect, the present invention relates to a connector that includes a fluid-seal fitting such as a male plug for mating with a cooperating connector, a mechanical fastener such as a screw thread for mating with the cooperating connector, and an outer housing positioned around the plug to form an annular space. The connector outer housing includes one or more vent openings for drainage and air-drying of any residual fluid in the annular space when the cap is plugged on. For example, the connector vent openings can be in an endwall of the outer housing, a peripheral sidewall of the outer housing, or both.

In another aspect, the invention relates to a sanitary cap that includes a fluid-seal fitting such as a male plug for mating with a lumen of the connector plug. The cap includes one or more vent openings for drainage and air-drying of any residual fluid in the annular space when the cap is plugged on. For example, the cap vent openings can be in an endwall body of the cap, a peripheral sidewall of the cap, or both. In some embodiments in which the cap vent openings are in the cap sidewall, they are formed by notches or recesses between segments of the cap sidewall, and in these or other similar embodiments mechanical stop surfaces are provided on the cap and the connector to limit to travel of the cap sidewall relative to the outer-housing sidewall to ensure that the cap vents remain open for ventilation.

These and other aspects, features, and advantages of the invention will be understood with reference to the drawing figures and detailed description herein, and will be realized by means of the various elements and combinations particularly pointed out in the appended claims. It is to be understood that both the foregoing general summary description and the following brief description of the drawings and detailed description of example embodiments are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description taken in connection with the accompanying drawing figures, which form a part of this disclosure. It is to be understood that this invention is not limited to the specific devices, methods, conditions, or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-9 show a vented connector 30 according to a first example embodiment of the invention, where the vented connector 30 includes a male plug or first connector portion 44. The connector 30 attaches to a medical fluid vessel 10 and mates with a cooperating connector or mating second connector 20 attached to an inline medical fluid vessel 12, with the connectors collectively forming a connector-set or coupling that detachably couples the vessels together for fluid flow therethrough. The connectors 20 and 30 can be made of conventional materials (e.g., as silicone or polyurethane) by conventional fabrication techniques and equipment (e.g., molding).

In the depicted embodiment, the vented connector 30 is attached to a vessel 10 that is a tube, though the term "vessel" is intended to be broadly construed to include any carrier or container for a fluid as well as any fluid-delivery device, and as such in other embodiments the vessel is a catheter, hose, bottle, bag, syringe, pump, or the like. As such, the connectors 20 and 30 can be used to couple together two vessels (with one vessel in/at the patient and the other vessel connected to an upstream medical fluid-delivery device such as a syringe) or to couple one vessel to a medical device (with one vessel in/at the patient and the other vessel being or a part of an upstream medical fluid-delivery device such as a syringe). In the depicted embodiment, the vented connector 30 is used for a vessel 10 for enteral feeding, with the term "vessel" in the "enteral feeding" context intended to be broadly construed to include not just feeding bags but also breast pumps, food bottles, other food-storage containers, extension sets, and the like. In the depicted embodiment, the vented connector 30 is an EN FIT connector for enteral feeding tubes, though in other embodiments the innovative features are included in connectors for fluid vessels for non-enteral and/or non-small-bore (medical or other) applications. And in the depicted embodiment, the vented connector 30 is a male connector and the cooperating connector 20 is a mating female connector, though in other embodiments this is reversed to provide a vented and/or capped female connector with an outer housing defining an annular space. In addition, the vented connector 30 is described herein for use with fluids, which as used herein means liquids and gases.

The connector 30 includes a vessel-attaching portion or tube engagement portion 32 defining a rear end 34, a coupling-attaching portion 36 defining a front end 38, and a lumen 40, e.g., a liquid passage, extending longitudinally therethrough from end to end. The vessel-attaching portion 32 attaches to (e.g., receives and secures) the vessel 10 and secures it in place with a good seal by conventional structures such as crimps or adhesives so that the vessel extends longitudinally from the rear end 34. The coupling-attaching portion 36 and the cooperating connector 20 detachably couple together mechanically by mating attachment fittings such as the depicted screw threads 42 and 22 (of the connector 30 and the cooperating connector 20, respectively) or other conventional mating mechanical fasteners as are known to persons of ordinary skill in the art such as bayonet fitting, snap-fit couplings, and the like. And the coupling-attaching portion 36 and the cooperating connector 20 sealingly mate together for fluid conveyance by mating male and female fittings such as the depicted male plug 44 and female receptacle 24 (of the connector 30 and the cooperating connector 20, respectively) or other conventional fluid-sealing structures as are known to persons of ordinary skill in the art such other friction fittings. In the depicted embodiment, the male plug 44 includes a peripheral wall that defines the lumen 40 extending axially all the way through it to convey the fluid through the connector 30. In some embodiments, the mating male and female seal fittings are designed to provide sufficient mechanical/frictional retention forces that the connectors 30 and 20 are securely coupled together and the connectors 30 and 20 thus do not include any separate screw threading or other mechanical fasteners.

In addition, the connector 30 includes an annular portion, i.e., outer housing 46 surrounding its plug 44, for example including a peripheral sidewall 48 and an endwall 50. The outer-housing sidewall 48 is arranged coaxially with and surrounding the plug 44 thereby forming an annular space 52 therebetween with an access opening at the front end 38 of the connector 30 (opposite the endwall). In this way, when the two connectors are coupled together with the male plug 44 of the connector 30 inserted into the female receptacle 24 of the cooperating connector 20, the peripheral sidewall or barrel 26 (defining the receptacle 24) of the cooperating connector 20 is coaxially received in the annular space 52 (between the outer-housing peripheral sidewall 48 and the plug 44) of the connector 30. And the connectors 30 and 20 can be coupled together by the screw threads 42 being inner threads on the outer-housing sidewall 48 (i.e., a threaded inner surface of the sidewall 48) and the mating threads 22 being outer threads on the receptacle sidewall 26, by mating threads between the plug and the receptacle sidewall, or by other threading arrangements. The outer-housing sidewall 48 of the connector 30 and the receptacle sidewall 26 of the cooperating connector 20 are typically generally cylindrical in shape and solid in structure (i.e., not fluid permeable).

The outer-housing endwall 50 extends at least partially between the outer-housing sidewall 48 and the plug 44, with at least one (e.g., two, as depicted) connecting portion or support 54 extending inwardly from the outer-housing sidewall to fix the outer-housing sidewall relative to the plug and thereby form the annular space 52. Typically each connecting portion or support 54 extends all the way between (e.g., radially, as depicted) and fixes together the outer-housing sidewall 48 and the plug 44. For instance, each connecting portion or support 54 includes a first section 54a extending from the annular outer-housing sidewall 48 radially toward the plug 44, and a second portion 54b extending from the first portion 54a to the plug 44. Each connecting portion or support 54 can form a handle configured to manipulate rotational movement of the connector 30 about an axis relative to the cooperating connector 20. To provide for fluid drainage and airflow ventilation, the outer-housing endwall 50 of the connector 30 includes at least one (e.g., two, as depicted) vent openings or apertures 56, i.e., drains, providing fluid communication between the annular space 52 and external to the annular space. The connector vent openings or apertures 56 can be in the form of two curved slots extending between two connecting portions 54 in the form of radial spokes, as depicted. Alternatively, the connector vent openings can be in the form of ports (e.g., holes in a circular, polygonal, frusto-conical, or other regular or irregular shape) extending axially through the endwall and/or radially through the outer sidewall, mesh openings in an endwall that is a mesh (e.g., a screen, grate, or lattice), or other types and arrangements of openings that provide for fluid drainage and airflow ventilation for the annular space. In addition, the outer-housing endwall 50 has an inner surface (partially defining the annular space 52) that can be sloped (ramped or taper, all or only part of it) toward the connector vent openings 56 to help direct fluid toward them.

In this way, any residual fluid from the vessels 10 and 12 that might otherwise be retained in the annular space 52 resulting in bacteria colonization will instead tend to drain out through the connector vent openings or apertures 56, i.e., drains, and be dried by airflow in and/or out of the vent openings. Furthermore, the connector vent openings 56 in the outer-housing endwall 50 provide better access to the annular space 52 for inspection and cleaning. Moreover, when the connector 30 is disconnected from the cooperating connector 20, a vacuum can form in the lumen 40 and induce a backflow of the fluid into the connector 30 and/or the cooperating connector 20, resulting in dosing inaccuracies, and the connector vent openings 56 can function to assist in breaking the vacuum to prevent fluid backflow and thus provide for more accurate dosing.

In addition, the connector 30 optionally includes a sanitary cap 70 for the lumen 40 at its front end 38 (opposite the attachment of the vessel 10). The cap 70 can be attached to the connector 30 by a tether 72 such as an integral length of material (as shown) or a cord, string, band, chain, or the like. In addition, the cap 70 can include a handle 73 for gripping to move the cap between its unplugged (see FIGS. 1-7) and plugged positions (see FIGS. 8-9). In the plugged position the cap 70 seals off the lumen 40 and the vessel 10 from outside contamination, which can be advantageous for example in enteral feeding applications in which the vessel 10 is inserted into the patient and left there for future feedings.

The cap 70 includes a body or endwall 74 with a seal fitting (e.g., a plug) 76 and a peripheral sidewall 78 axially extending from it. The cap body/endwall 74 is typically a solid member such as a panel for sealing the annular space when capped. And the cap sidewall 78 can be a solid peripheral member such as a collar or flange, or two or more peripherally arranged prongs such as fingers or tabs, for reception and retention in the annular space when capped. In the plugged position, the cap plug 76 is received in the connector-plug lumen 40 at its front end 38 with a snug fit for sealing to prevent the escape of fluids from the vessel 10. And the cap sidewall 78 is received in the annular space 52 through its access opening so that it engages the connector 30 with a snug fit for mechanical/frictional retention to removably secure the cap 70 in place in the plugged position. In other embodiments, the cap seal fitting is a sleeve, recess, or other structural element that mates with the connector seal fitting to seal the lumen closed. And in yet other embodiments, the cap 70 and the connector 30 additionally or alternatively include mating screw threads or other fasteners for removably securing the parts together.

To provide for fluid drainage and airflow ventilation of the annular space 52 when the cap 70 is the plugged position, the cap includes at least one (e.g., three, as depicted) vent openings 80 providing fluid communication between the annular space and external to the annular space. The cap vent openings 80 can be in the form of one or more notches defined by gaps between one or more segments of the cap sidewall 78, for example the three curved notches between the three segments of the cap sidewall formed by the undulating edge of the cap sidewall, as depicted. Alternatively, the cap vent openings can be in the form of ports (e.g., holes in a circular, polygonal, conical, or other regular or irregular shape) extending axially through the cap body/endwall and/or radially through the cap sidewall, mesh openings in a portion of the cap body that is a mesh (e.g., a screen, grate, or lattice), or other types and arrangements of openings that provide for fluid drainage and airflow ventilation for the annular space with the cap in the plugged position.

In this way, any residual fluid from the vessels 10 and 12 that might otherwise be retained in the annular space 52 (upon disconnection of the connectors 30 and 20) resulting in bacteria colonization will instead tend to drain out through the cap vent openings 80 and be dried by airflow in and/or out of the vent openings. Furthermore, the cap vent openings 80 can facilitate better inspection and cleaning of the annular space 52. Moreover, the connector vent openings 56 and the cap vent openings 80, in combination with the annular space 52, form a continuous passageway (see FIG. 9) for airflow to enter the annular space at one end and exit the other end for enhanced drying and to prevent an airlock that might restrict airflow in and out of the annular space. As such, as used herein reference to connector outer-housing vent openings being "at the outer-housing endwall" includes the vent opening being formed in or by the outer-housing endwall 50 as well as being formed in or by the outer-housing sidewall 48 but immediately adjacent the outer-housing endwall to provide the continuous airflow passageway along substantially the entire length of the annular space 52.

In addition, to make sure that the cap vent openings 80 are at least partially exposed and uncovered (sufficiently for functioning for their intended purpose as described herein)

when the cap 70 is in the plugged position on the connector 30, engaging stop surfaces 58 and 82 can be provided on the connector and the cap, respectively, to define (and thus limit) the how far the cap fits onto the connector. In the depicted embodiment, for example, the connector stop surface 58 is formed by a rim of the connector plug 44 defining the lumen 40, and the cap stop surface 82 is formed by a base of the cap plug 76. As can be seen for example in FIGS. 8-9, in the plugged position the cap vent openings 80 are partially covered but still partially exposed to permit fluid flow therethrough. Alternatively, the connector and cap stop surfaces can be formed by at least one inward-extending member (e.g., a collar, flange, rib, tab, or the like) of the outer-housing sidewall and by the rear (insertion) ends of the cap sidewall segments, respectively, so the inward-extending members limit how far into the annular space the cap sidewall segments can be inserted. Further alternatively, the connector stop surface can be in the form of an endwall, collar, flange, rib, tab, or the like on or adjacent the connector plug and/or lumen (e.g., within the lumen), and/or the cap stop surface can be in the form of a skirt, collar, flange, rib, tab, wing, or the like on or adjacent the cap plug.

It should be noted that the depicted embodiment includes the connector vent openings 56 and the cap vent openings 80 in combination, while other embodiments include only one of these two features. Furthermore, it should be noted that some embodiments include connector vent openings in the outer-housing sidewall as an addition or alternate to the depicted connector vent openings 56 in the outer-housing endwall 48, while other embodiments include cap vent openings in the cap endwall as an addition or alternate to the depicted cap vent openings 80 in the cap sidewall 78. As such, any of the vent openings disclosed herein can be implemented individually or in any combination with any other vent opening(s) disclosed herein or not disclosed herein.

Figure 1:
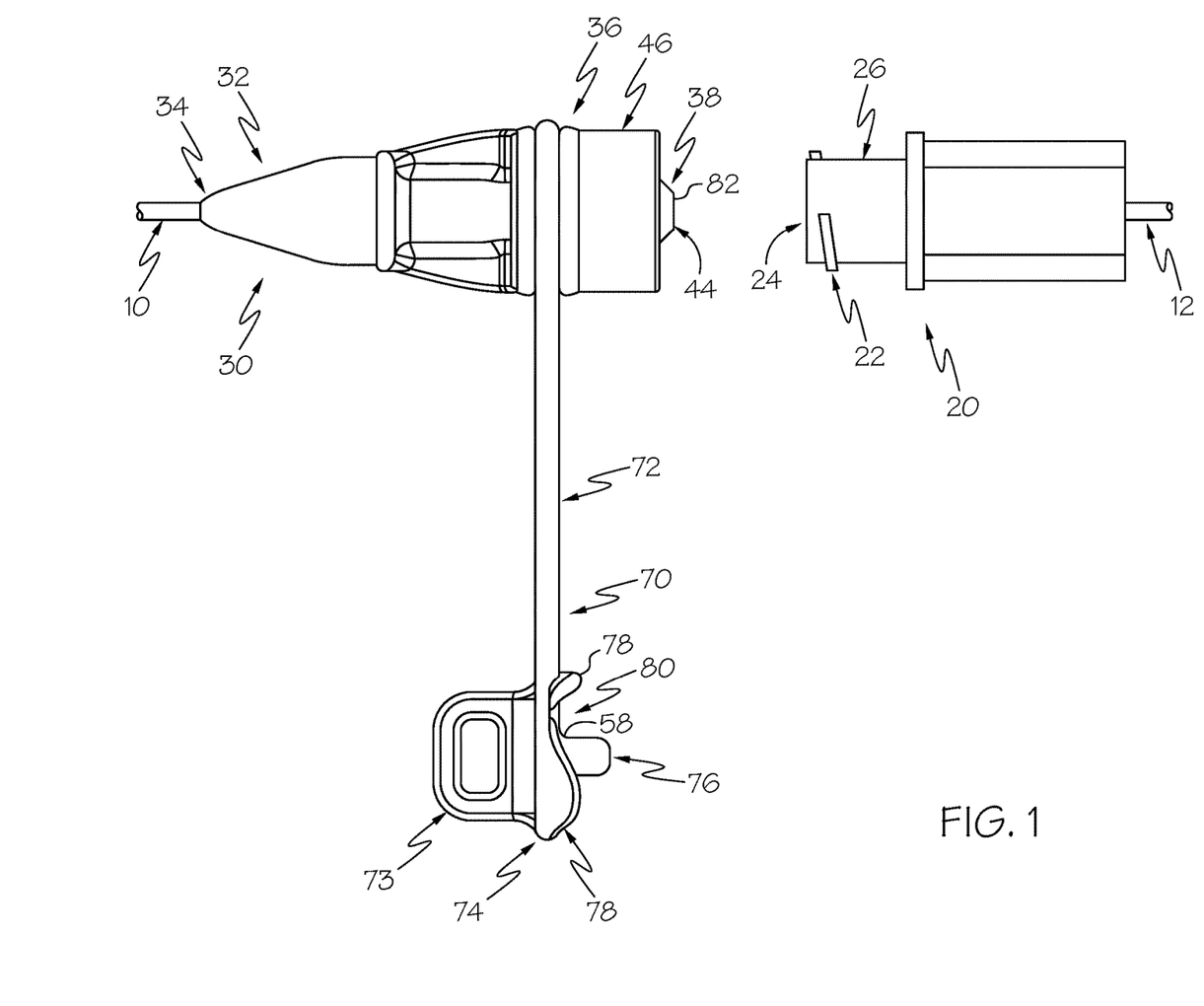
FIG. 1 is a side view of a vented male connector according to a first example embodiment of the present invention, shown with a mating female connector and with its cap unplugged so that it's ready for connection to the mating female connector.
Figure 2:
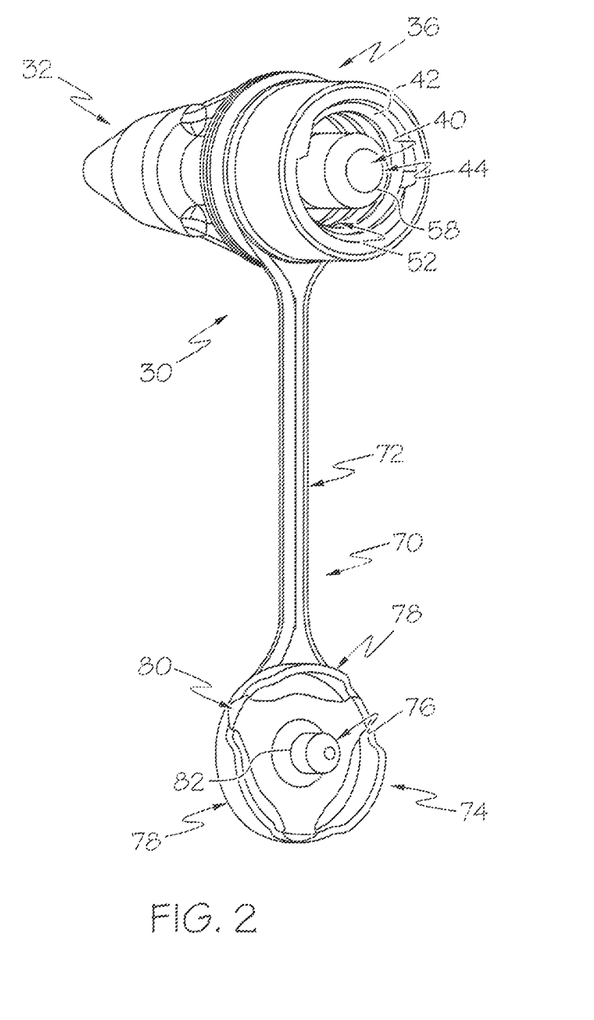
FIG. 2 is a front perspective view of the male connector of FIG. 1.
Figure 3:
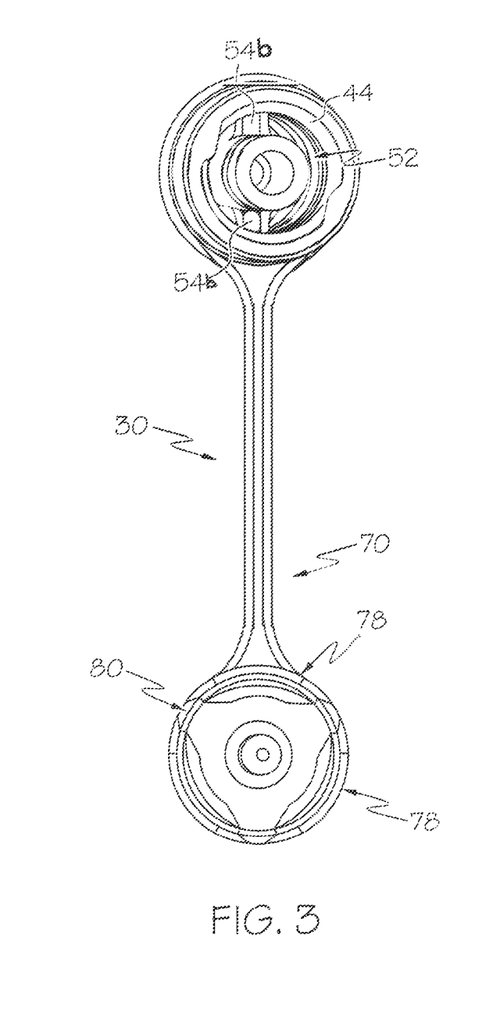
FIG. 3 is another front perspective view of the male connector of FIG. 1.
Figure 4:
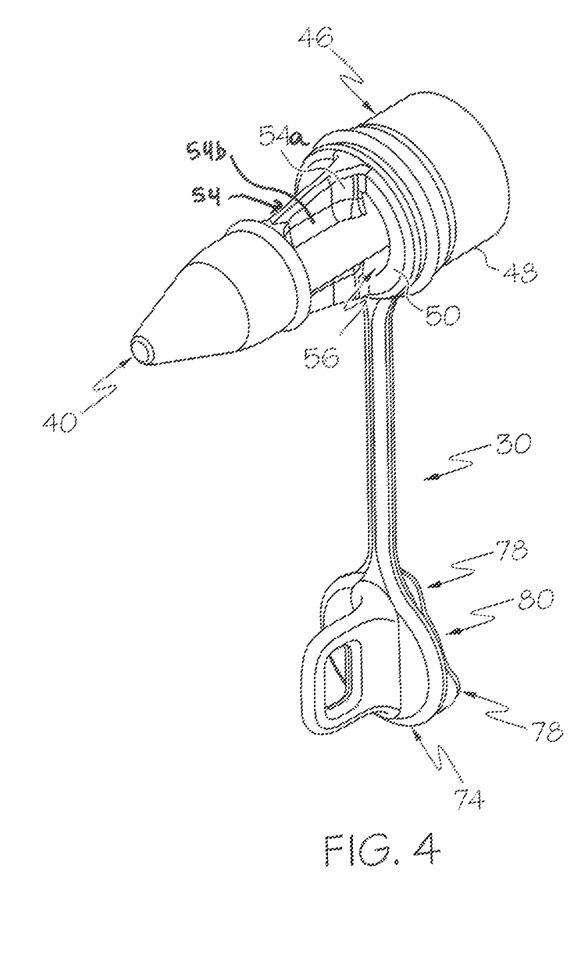
FIG. 4 is a rear perspective view of the male connector of FIG. 1.
Figure 5:
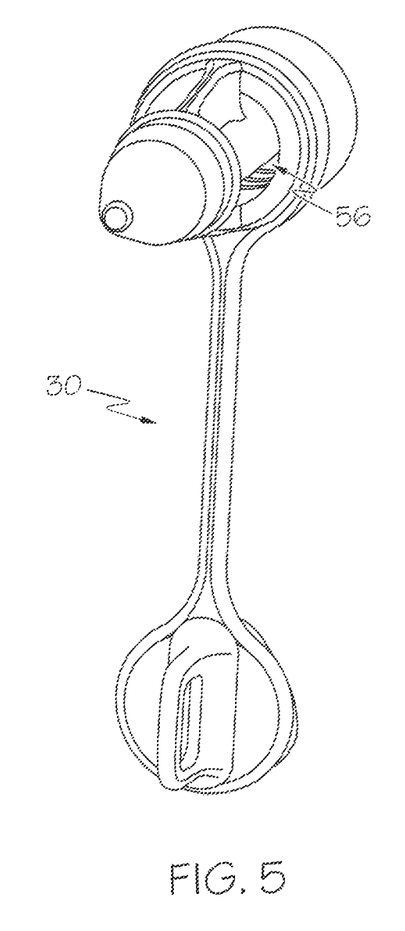
FIG. 5 is another rear perspective view of the male connector of FIG. 1.
Figure 6:
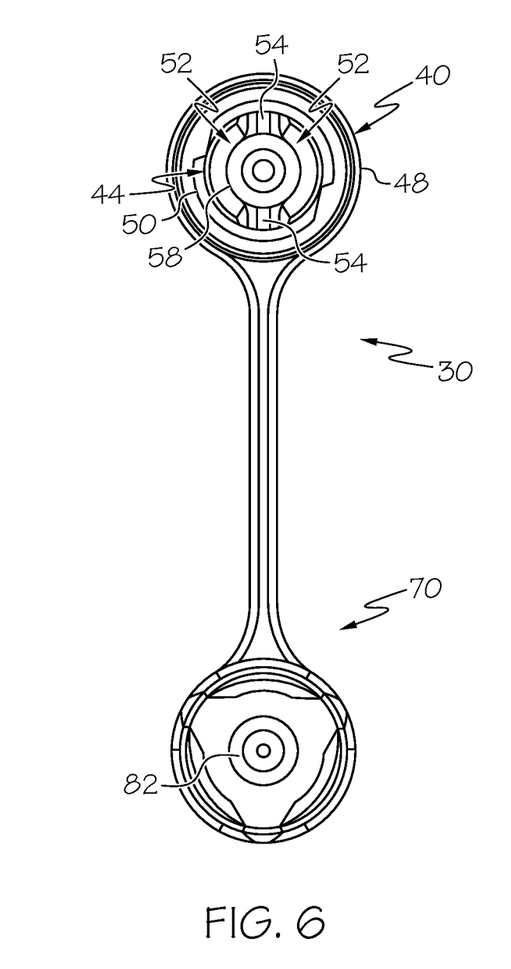
FIG. 6 is a front view of the male connector of FIG. 1.
Figure 7:
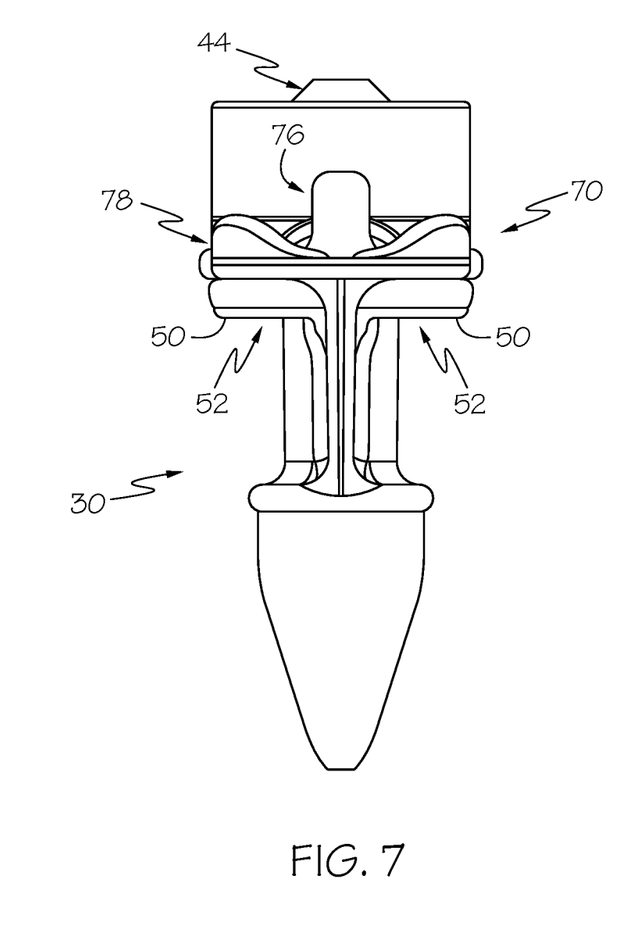
FIG. 7 is another side view of the male connector of FIG. 1.
Figure 8:
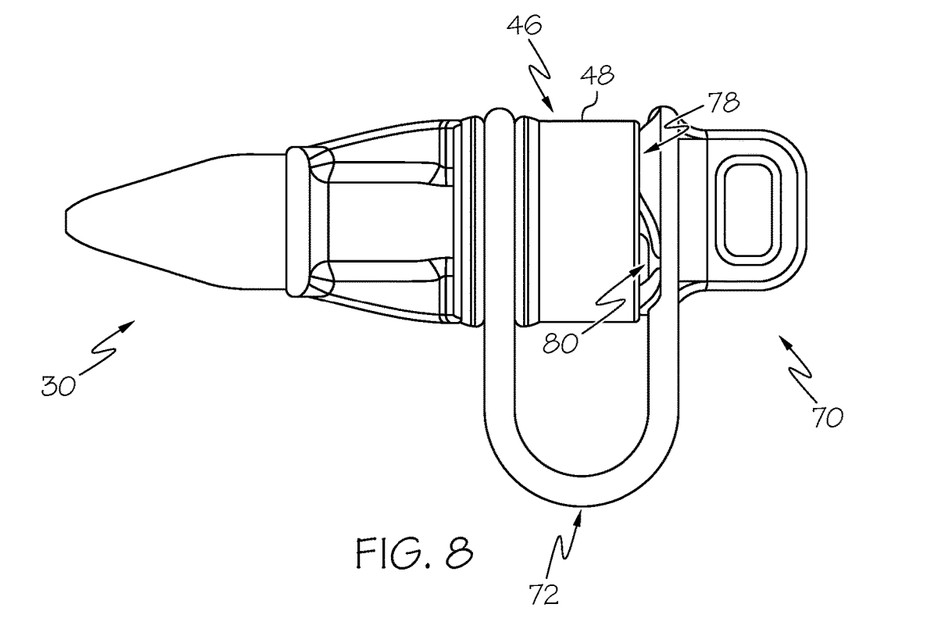
FIG. 8 shows the male connector of FIG. 1 with its cap in a plugged position.
Figure 9:
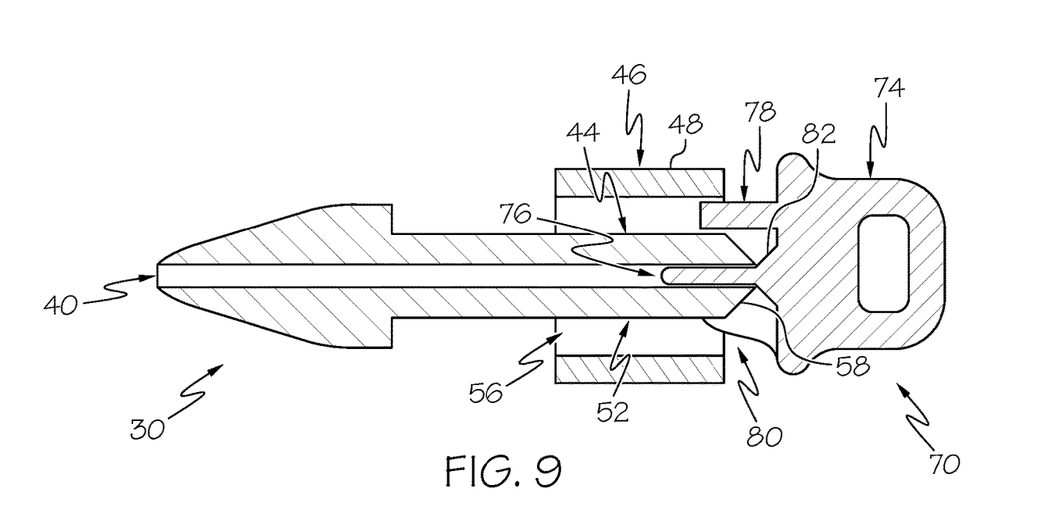
FIG. 9 is a cross-sectional view of the male connector of FIG. 8 showing a ventilation passageway for airflow through the connector with its cap in a plugged position.
Figure 10:
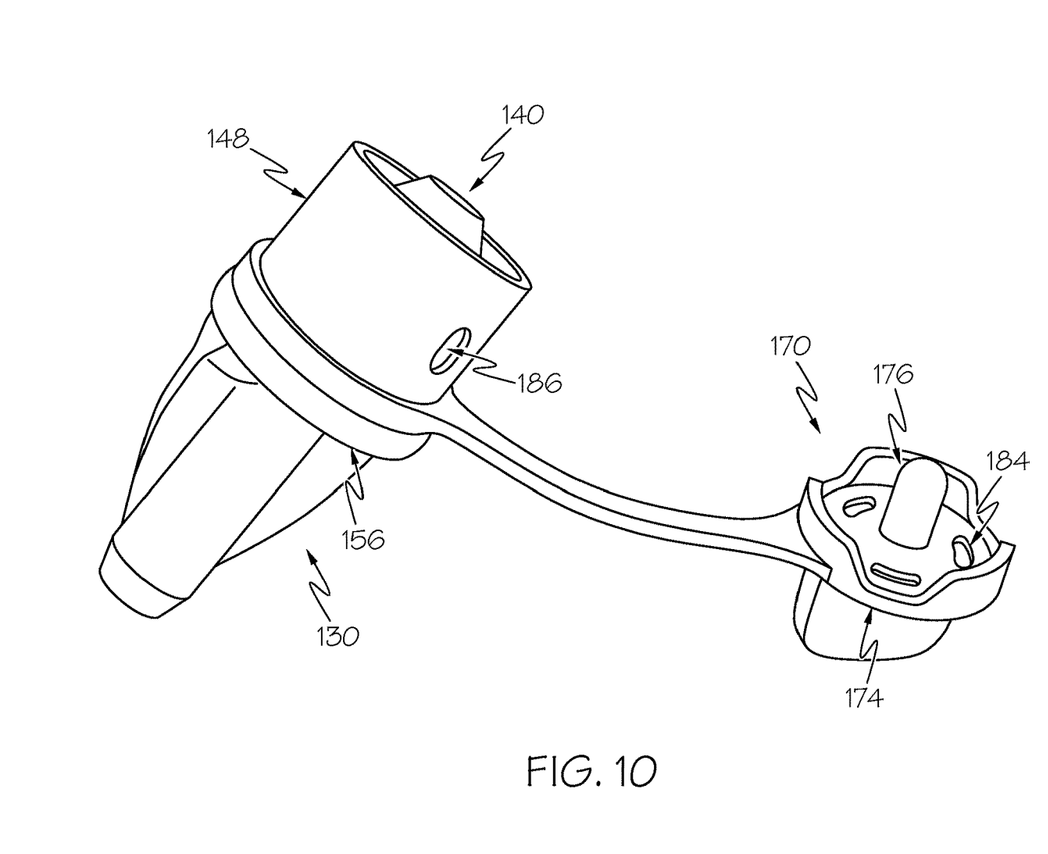
FIG. 10 is a perspective view of a vented connector according to a second example embodiment, shown with its cap unplugged so that it's ready for connection to a mating female connector.

FIG. 10 shows a vented connector 130 according to a second example embodiment of the present invention. The vented connector 130 is substantially similar to that of the first example embodiment described above, with exceptions as noted herein. In this embodiment, for example, the connector 130 includes one or more vent openings 186 formed in the outer-housing sidewall 148, in addition to the one or more vent openings 156 formed in the outer-housing endwall (not shown) described above. The connector vent openings 186 in the outer-housing sidewall 148 provide for drainage and drying, vacuum breaking, and enhanced inspection and cleaning similarly to the venting in the first example embodiment.

In the depicted embodiment, the connector vent openings 186 are generally circular in shape, though in other embodiments the vent openings can have an oval, polygonal, conical, or other regular or irregular shape. The depicted connector vent openings 186 are positioned sufficiently away from the front/cooperating connector end of the connector 130 that they are not blocked by the cap sidewall segments when the cap 170 is plugged onto the connector (with the cooperating connector detached). In other embodiments, the vent openings are provided with deflectors (e.g., V-shaped members extending inward from the inner surface of the outer-housing sidewall and positioned between the vent openings and the front end) that are engaged by and induce rotation of the cap sidewall segments when the cap is plugged onto the connector so that the vent openings align with the cap sidewall vent openings. And in still other embodiments, an array or series of the sidewall vent openings are provided.

In addition, the cap 170 can have one or more vent openings 184 axially formed in the cap body or endwall 174. The cap vent openings 184 are positioned radially outward from the cap plug 176 so that when the cap 170 is plugged onto the connector 130 they provide ventilation to the annular space 152 but they do not provide ventilation to the lumen 140. The cap vent openings 184 can be in the form of curved slots (as depicted) or they can have a circular, polygonal, conical, or other regular or irregular shape. In other embodiments, the connector 120 includes only the cap vent openings 184 or only the connector vent openings 186.

Figure 11:
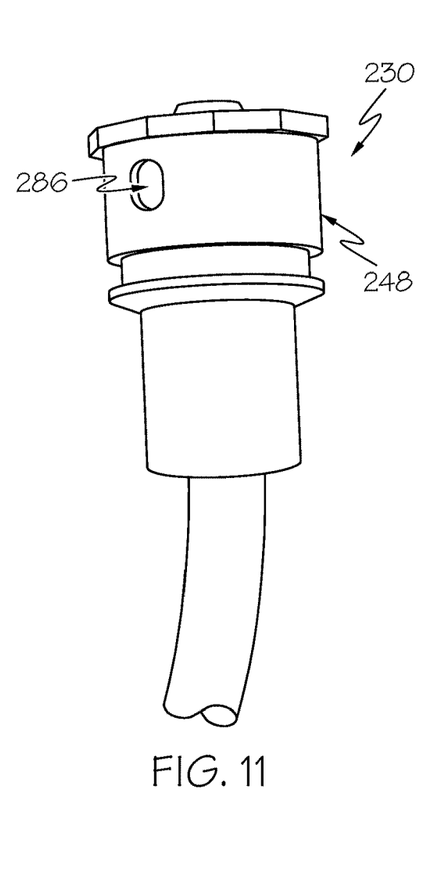
FIG. 11 is a perspective view of a vented connector according to a third example embodiment, shown without its cap.

FIG. 11 shows a vented connector 230 according to a third example embodiment of the present invention. The vented connector 230 is substantially similar to those of the first and second example embodiments described above, with exceptions as noted herein. In this embodiment, for example, the connector 230 includes the one or more vent openings 286 formed in the outer-housing sidewall 248, but not any vent openings formed in the outer-housing endwall. The connector vent openings 286 in the outer-housing sidewall 148 provide for drainage and drying, vacuum breaking, and enhanced inspection and cleaning similarly to the venting in the first and second example embodiments. It should be noted that the connector 230 is depicted without a cap, though in some embodiments a cap is provided, and the cap can include cap vent openings as described herein as an addition or alternate to the connector vent openings 286.

While the invention has been described with reference to preferred and example embodiments, it will be understood by those skilled in the art that a variety of modifications, additions and deletions are within the scope of the invention, as defined by the following claims.

What is claimed is:

1. A medical tubing connector comprising:
   a first connector portion configured for connecting to a mating second connector;
   a tube engagement portion integral with and opposite the first connector portion and configured for connecting to a medical tube;
   a liquid passage extending along an axis through the first connector portion and the tube engagement portion, the first connector portion including a continuous outer surface for sealing engagement with the mating second connector;
   an annular portion integral with and surrounding the first connector portion, the annular portion comprising a threaded inner surface; and
   a connecting portion connecting the first connector portion to the annular portion, the connecting portion including a discontinuity permitting liquid to pass through the connecting portion so that liquid is prevented from pooling between the first connector portion and the annular portion;
   wherein the connecting portion is defined by spaced apart connecting supports extending between the first connector portion and the annular portion, wherein the spaced apart connecting supports comprise handles configured to manipulate rotational movement of the first connector portion about an axis with respect to the mating second connector, each connecting support comprising a first section extending from the annular portion and a second section projecting from the first section and extending from the first section to the first connector portion, the second section engaging the first connector portion at a location radially spaced apart from the location at which the first section extends from the annular portion.

2. The medical tubing connector of claim 1, wherein the connecting portion discontinuity comprises a drain.

3. The medical tubing connector of claim 1, wherein the connecting portion discontinuity comprises at least one aperture.

4. The medical tubing connector of claim 1, wherein the connecting portion discontinuity comprises at least one slot.

5. The medical tubing connector of claim 1, wherein the annular portion comprises a collar concentrically oriented about the first connector portion.

6. The medical tubing connector of claim 1, wherein the first connector portion extends to a distal end outside the annular portion.

7. The medical tubing connector of claim 1, wherein the first connector portion, the connecting portion, and the annular portion are formed as one piece of material.

8. The medical tubing connector of claim 1, wherein the connecting portion defines a drain permitting liquid to pass through the connecting portion so that liquid is prevented from pooling between the first connector portion and the annular portion.

9. The medical tubing connector of claim 1, wherein the first connector portion extends to a distal end outside the annular portion.

10. A medical tubing connector comprising:
   a male plug configured for connecting to a cooperating connector;
   a vessel-attaching portion integral with and opposite the male plug and configured for connecting to a medical tube;
   a lumen extending along an axis through the male plug and the vessel-attaching portion, the male plug including a continuous outer surface for sealing engagement with the cooperating connector;
   an outer housing integral with and surrounding the first connector portion, the outer housing comprising an outer housing sidewall having inner screw threads; and
   a connecting portion connecting the male plug to the outer housing, the connecting portion including a discontinuity permitting liquid to pass through the connecting portion so that liquid is prevented from pooling between the male plug and the outer housing;
   wherein the connecting portion is defined by spaced apart connecting portions extending between the male plug and the outer housing, wherein the spaced apart connecting portions comprise handles configured to manipulate rotational movement of the male plug about an axis with respect to the cooperating connector, each spaced apart connecting portion comprising a first section extending from the outer housing and a second section projecting from the first section and extending from the first section to the male plug, the second section engaging the male plug at a location radially spaced apart from the location at which the first section extends from the outer housing.

11. The medical tubing connector of claim 10, wherein the connecting portion discontinuity comprises at least one vent.

12. The medical tubing connector of claim 10, wherein the outer housing comprises a collar concentrically oriented about the male plug.

13. The medical tubing connector of claim 10, wherein the male plug extends to a distal end outside the outer housing.

14. The medical tubing connector of claim 10, wherein the male plug, the connecting portion, and the outer housing are formed as one piece of material.

15. The medical tubing connector of claim 10, wherein the connecting portion defines a vent permitting liquid to pass through the connecting portion so that liquid is prevented from pooling between the male plug and the outer housing.

* * * * *